United States Patent [19]
Herron

[11] Patent Number: 6,126,129
[45] Date of Patent: Oct. 3, 2000

[54] APPARATUS AND METHOD FOR SUPPORTING AN INTRAVENOUS SOLUTION CONTAINMENT VESSEL

[76] Inventor: Terry Herron, Escondido Box 101J, Del Rio, Tex. 78840

[21] Appl. No.: 09/216,517

[22] Filed: Dec. 18, 1998

[51] Int. Cl.⁷ ........................................... A47K 1/08
[52] U.S. Cl. ............................ 248/311.3; 248/309.1; 222/105
[58] Field of Search ................. 248/310, 311.3, 248/312, 309.1; D9/455; D24/108; 222/105

[56] References Cited

U.S. PATENT DOCUMENTS

| | | | |
|---|---|---|---|
| D. 410,846 | 6/1999 | Leong et al. | D9/455 |
| 1,290,809 | 1/1919 | Truax | 248/311.3 |
| 2,056,096 | 9/1936 | Etter | 221/62 |
| 3,395,882 | 8/1968 | Marshall | 248/318 |
| 4,030,690 | 6/1977 | Hanauer et al. | 248/311.3 |
| 5,143,337 | 9/1992 | Tomayko, Jr. et al. | 248/311.2 |
| 5,257,765 | 11/1993 | Halle | 248/222.1 |
| 5,649,643 | 7/1997 | Ridgeway | 222/105 |

FOREIGN PATENT DOCUMENTS 1174943  7/1964  Germany ............................. 248/311.3

Primary Examiner—Ramon O. Ramirez
Assistant Examiner—Walter Landry
Attorney, Agent, or Firm—Jenkens & Gilchrist, A Professional Corporation

[57] ABSTRACT

An apparatus and method for supporting an intravenous containment vessel is disclosed. The apparatus comprises an elongated elliptical or circular sleeve which is generally open at its upper end and generally closed at its lower end. Left and right guide members in the front of the sleeve cooperate to form an opening along the sleeve which terminates at a convergent end. The apparatus also comprises a base which has a throat aligned with the convergent end. The containment vessel, having a spout, is usually placed within the sleeve, so that the spout rests at the throat. The support apparatus can be attached to a stand or other location using integral support mounting means.

22 Claims, 4 Drawing Sheets

APPARATUS AND METHOD FOR SUPPORTING AN INTRAVENOUS SOLUTION CONTAINMENT VESSEL

BACKGROUND OF THE INVENTION

1. Technical Field

This invention relates generally to an apparatus and method for supporting a fluid dispensing means. More particularly, the present invention relates to a method and apparatus for supporting an intravenous (IV) solution containment vessel, such as a bag or a bottle.

2. History of Related Art

Support holders for intravenous infusion bottles and bags are well known in the art. Generally, those holders for bottles comprise some type of clamp or buckle mechanism which serves to secure the bottle during suspension from some type of hook or bracket. These holders generally operate by exerting physical friction force against the outer surface of the bottle and provide a loop for hanging from a hook or, in the case of a single strap, some type of fixed mount to a wall or an IV stand.

IV bags are preferred over bottles because they are cheaper to make, safer, and may be stored more densely. However, the use of a strap or friction holding mechanism against a plastic bag filled with fluid is problematic. The most popular support apparatus provides some type of convoluted hook mechanism from which the upper end of the bag may be directly suspended. This assumes the inclusion of a reinforced hole at the upper end of the bag through which the hook can be inserted.

The prior art holding devices, whether made of clamping mechanisms that depend on friction against the side of a bottle, or alternatively, using convoluted hooks which are applied to plastic bags, share a similar problem. Any type of clamp or strap requires a two-handed approach to securing the bottle for use. However, in emergency situations, the medical technician or doctor is often in a hurry and extra time required to secure the IV bottle within a strap is time which could otherwise be spent saving a patient's life. The same is true for plastic bags suspended from hooks; the hook is often constructed so that the bag is not easily dislodged from the end. However, such convoluted construction again serves to delay the attachment of the bag to the hook and requires two hands on the part of the user. In the case of either type of holder, the attachment mechanism for IV stands and/or walls has not been standardized, and may cause further delay by unfamiliar users.

Therefore, what is needed is a standard holder or support apparatus which can be used for both IV bottles and bags that requires only a single-handed operation to secure the bottle/bag for use. Further, the support apparatus should be constructed so as to resist dislodging the bottle/bag due to accidental bumps or blows. The support apparatus should also be constructed so as not to damage the bottle/bag, and further, to protect the suspended containment vessel and its contents from injury. The support apparatus should also provide the advantages of easy replacement for the bottle/bag, and easy, standardized attachment to IV stands and/or walls. Finally, a support apparatus which can be molded from a single piece of plastic, so as to be made inexpensively, and having no moving parts, is also desirable.

SUMMARY OF THE INVENTION

One embodiment of the IV support apparatus of the present invention comprises an elongated elliptically-shaped sleeve which is generally open at its upper end. The sleeve has a front, a back with support mounting means, and a lower end spaced from the upper end. The sleeve front has left and right guide members, each with a lower end disposed at the lower end of the sleeve, the guide members extending from the upper end to the lower end of the sleeve so as to terminate in a convergent end. The apparatus also comprises a generally closed base which intersects with the front, the back, and the lower ends of the left and right guide members, the base having an open throat portion aligned with the convergent end of the longitudinal opening.

The apparatus may also comprise an elongated circular sleeve constructed along the same lines as the elliptical sleeve. While the elliptical sleeve is formed to better accommodate IV bags, which are generally manufactured in the shape of a bulbous rectangle, the circular sleeve better accommodates IV bottles, which are generally manufactured in the shape of a right circular cylinder. In either case, the throat, which represents an opening in the base, accommodates the spout from either the IV bag or IV bottle.

The method of the present invention for supporting an intravenous containment vessel, which may be an IV bottle or IV bag, includes the step of attaching an intravenous support apparatus to an IV stand (the apparatus having the characteristics described above, wherein the apparatus has a support mounting means which allows fixed attachment to the IV stand). Once the IV support apparatus is attached to the IV stand, the IV containment vessel, which has a spout, is placed into the sleeve using a single hand to guide the spout between the left and right guide members of the apparatus. The spout is then placed so as to rest against the throat.

The support apparatus may be mounted using the support mounting means, such as holes or slots which are cut into the back of the sleeve. Screws or other commonly available fasteners may also be used to fixedly attach the sleeve to an IV stand, a wall, a bed, or other desired location. An alternate mounting means comprises a single hole near the upper end of the sleeve which can be used to hang the apparatus from a conventional IV stand, or another suitable hook/hanger.

BRIEF DESCRIPTION OF THE DRAWINGS

A more complete understanding of the structure and operation of the present invention may be had by reference to the following detailed description when taken in conjunction with the acing drawings, wherein.

DETAILED DESCRIPTION OF PRESENTLY PREFERRED EXEMPLARY EMBODIMENTS

Figure 1:
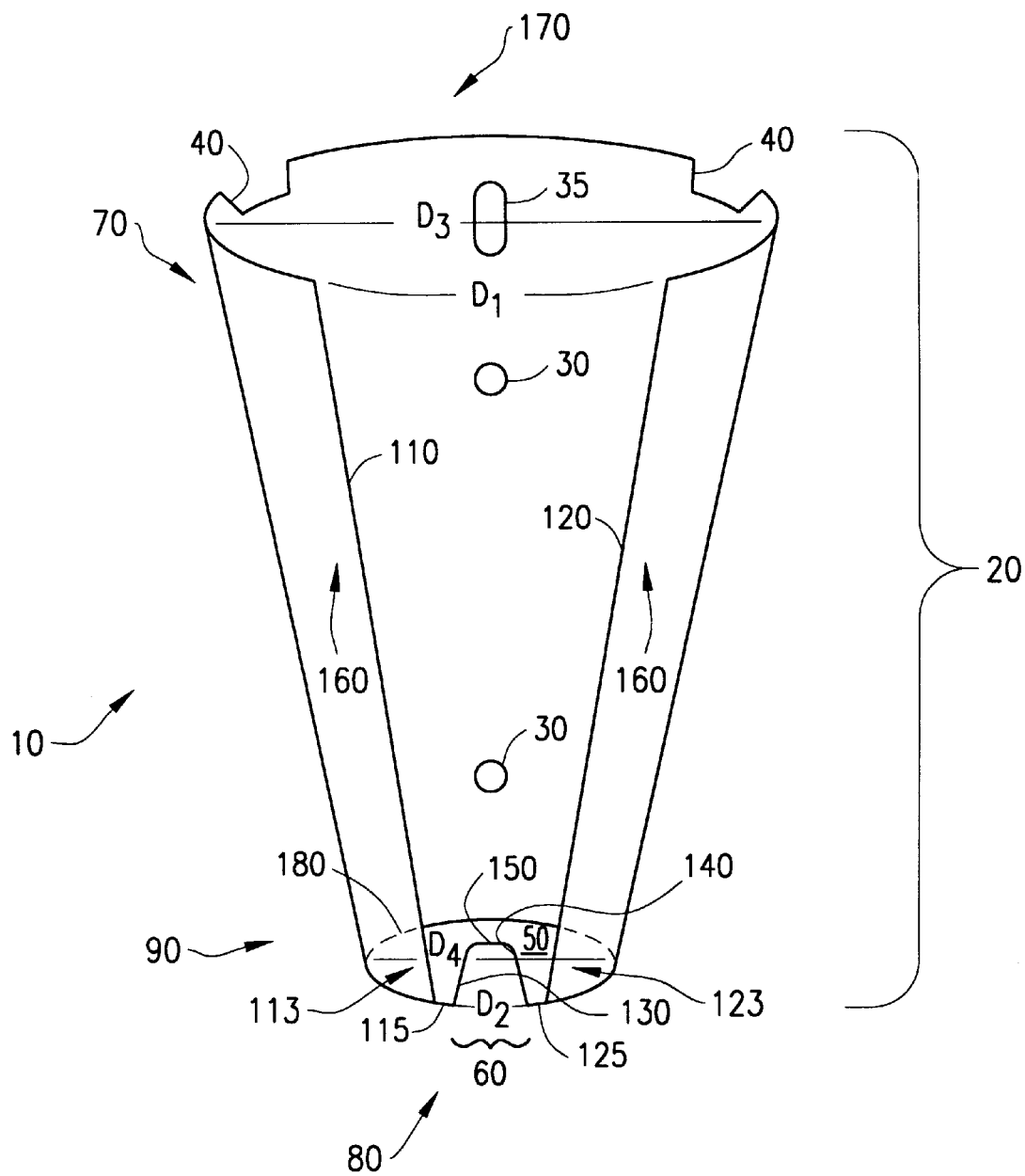
FIG. 1 is a perspective view of one embodiment of the present invention.

Turning now to FIG. 1, a perspective view of one embodiment of the apparatus of the present invention can be seen. The IV support apparatus 10 of the present invention comprises an elongated, hollow, generally elliptical sleeve 20 having support mounting means 30 located along the back 170 of the sleeve 20. The support mounting means 30 may comprise holes or slots which allow screws or other commonly available fasteners to provide for fixed attachment to an IV stand, a wall, a bed, or other desired location. The support mounting means 30 may also comprise snaps or hooks attached to the back 170 of the sleeve 20, so as to mate with corresponding fastening means, such as snaps, or holes, which have been previously located at some desired location. In any event, the support mounting means should be designed so as to render the sleeve 20 relatively immobile and impervious to accidental blows or bumps. The support mounting means 30 should also be strong enough to withstand the full weight of an intravenous fluid containment vessel 220, such as an IV bag or IV bottle, when it is placed within the sleeve 20 (See FIG. 6).

The sleeve 20 may be constructed from a variety of materials, including aluminum, stainless steel, plastic, fiberglass, or ceramic/polymer combinations. The material chosen will depend on design choice trade-offs between cost, flexibility, durability and ease of cleaning. The most desirable materials include clear acrylic or polycarbonate.

An alternate mounting means 35 may comprise hole or slot cut into the back 170 of the sleeve 20 which can be used to hang the support apparatus 10 from a convenient hook, such as those used on conventional IV stands. This allows the use of the support apparatus 10 in locations which were not originally designed to accommodate the support mounting means 30. Also, such alternate mounting means 35 provide the opportunity to move the support apparatus 10 from one location to another with ease. Other possibilities for implementing the alternate mounting means 35 include snaps or hooks attached to the back 170, as described above. Suction cups with embedded hooks may also be applied as an alternate mounting means 35.

The elongated, generally elliptical sleeve 20, which has a front 160, generally comprises an open upper end 70, and a lower end 90 spaced from the upper end 70. A longitudinal opening in the front 160 of the sleeve 20 is formed by the cooperation of left and right guide members 110 and 120, extending from the upper end 70 to the lower end 90, and converging in a convergent end 80 disposed at the lower end 90 of the sleeve 20. The left guide member 110 has a left guide member lower end 113, and the right guide member 120 has a right guide member lower end 123; each of the guide member lower ends 113 and 123 is also disposed at the lower end 90 of the sleeve 20.

Figure 3:
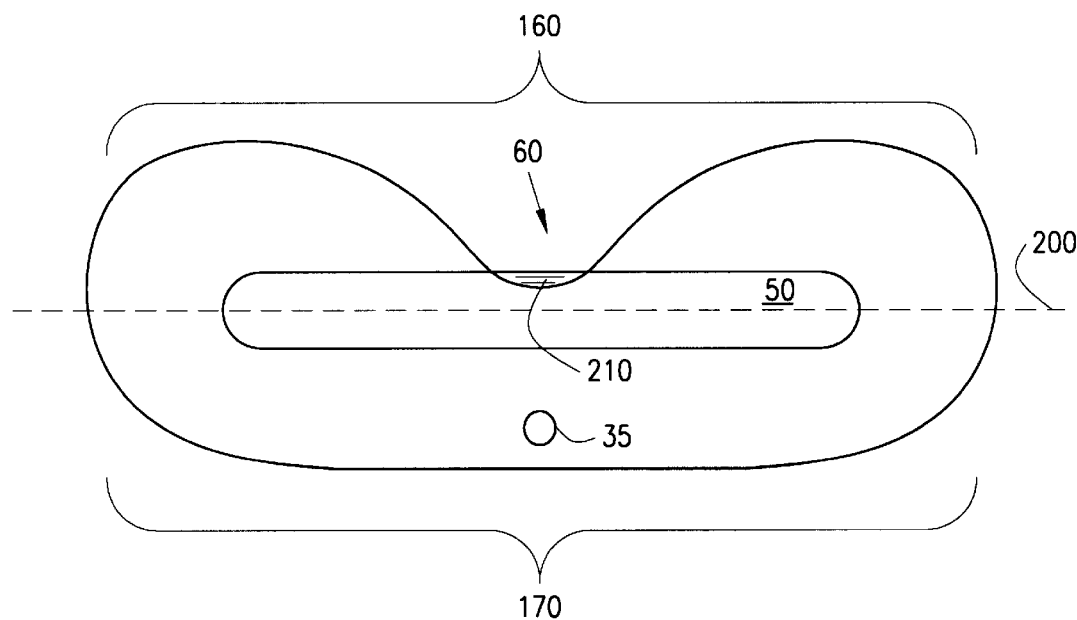
FIG. 3 is a bottom view of one embodiment of the present invention.
Figure 4:
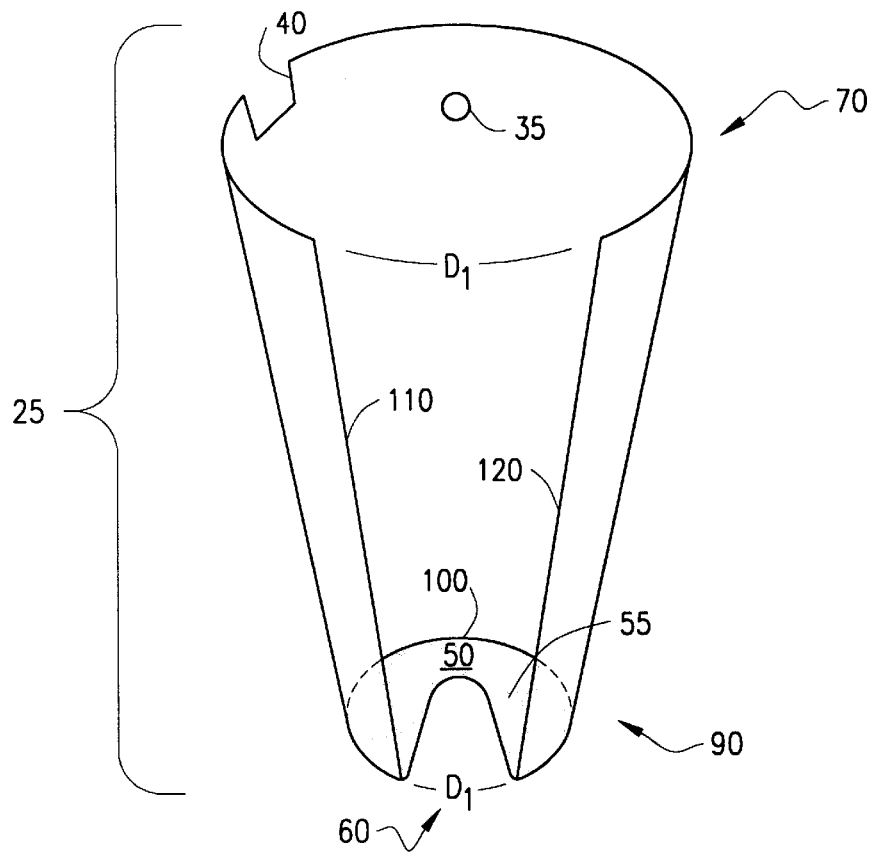
FIG. 4 is a perspective view of an alternative embodiment of the present invention.

The apparatus 10 also has a generally closed base 50 which intersects the front 160, the back 170, and the lower ends of the left and right guide members 113 and 123. The base 50 has an open throat 60 portion aligned with the convergent end 80 of the longitudinal opening in the sleeve 20. As seen in FIG. 1, the base 50 is disposed substantially perpendicular to the sleeve 20, and has a generally elliptical form. However, other implementations of the base 50 are possible, and may even be desirable, depending on the specific use of the apparatus 10. For example, the base 50 may be disposed substantially perpendicular to the sleeve 20, but may have a generally circular form, as is illustrated in FIG. 4. The base 50 may also have a generally linear form, wherein the throat portion 60 is disposed at the convergent end 80 of the longitudinal opening, as illustrated in FIG. 3. In each of the alternative forms, the open throat 60 portion of the base 50 is continuous with the substantially symmetrical and convergent end 80 of the longitudinal opening in the front of the sleeve 20 to form a substantially symmetrical means for centering the spout of the IV bag or bottle such that the spout will fall between the sides of the longitudinal opening in the front of the sleeve 20 and continue through the open throat 60 portion at the convergent end 80 of the sleeve 20.

Returning to FIG. 1, the throat 60 is bordered by left and right throat members 130 and 140, and the throat back 150. The intersection of the left throat member 130 with the lower end of the left guide member 113 is located at the left guide point 115, while the intersection of the right throat member 140 with the lower end of the right guide member 123 is located at the right guide point 125.

The distance between the left and right guide members at the upper end 70 "$D_1$" is generally greater than the distance "$D_2$" at the lower end 90, as measured between the left guide point 115 and the right guide point 125. Likewise, the distance between the left and right guide members at the upper end 70 along "D3" is generally greater than the distance along "D4" at the lower end 90. Thus, the guide members 110, 120 may slant inwardly toward the back 170 from the upper end 70 to the lower end 90 (i.e. inwardly slanting guide members 110, 120).

Figure 2:
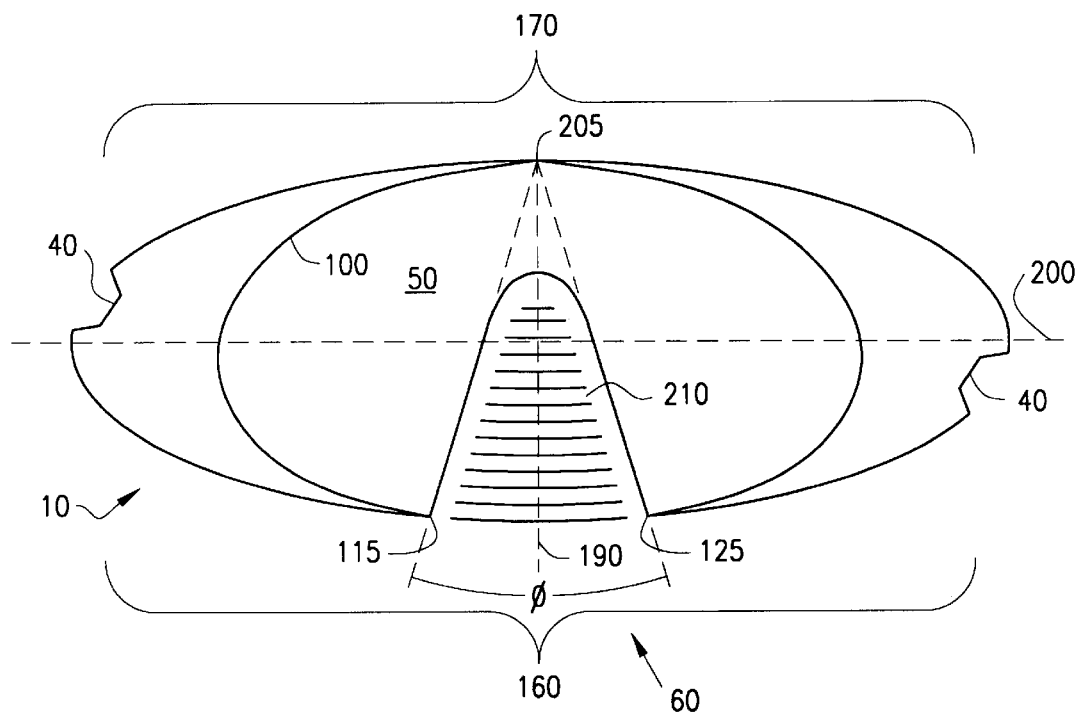
FIG. 2 is a top view of one embodiment of the present invention.

Turning now to FIG. 2, a top view of the support apparatus 10 can be seen. Most particularly to be noted in this figure is the existence of a minor base central axis 190, which bisects the area of the base 50 along a line running from between the left and right guide points 115 and 125 to the center of the back 170 of the sleeve 20. A major base central axis 200 also bisects the area of the base 50 and runs along a line perpendicular to the minor base central axis 190. An apex 205, located at the intersection of the minor base central axis 190 and the elliptical base intersection 100, defines an angular arc "$\phi$", which is further defined by the lines running from the apex 205 through the left and right guide points 115 and 125. This angular arc $\phi$ is preferably from about five degrees to about ninety degrees, but is more preferably about sixty degrees. The distance $D_2$ can be roughly defined in proportion to the width of the sleeve 20 and the depth of the sleeve 20 (as measured along the major and minor base central axes 190 and 200, respectively), and when the angular arc $\phi$ measures approximately sixty degrees, provides the best performance. As a further performance determination, the distance $D_1$ is preferably about two to about eight times greater than the distance $D_2$, but is most preferably about four times greater than the distance $D_2$.

Figure 6:
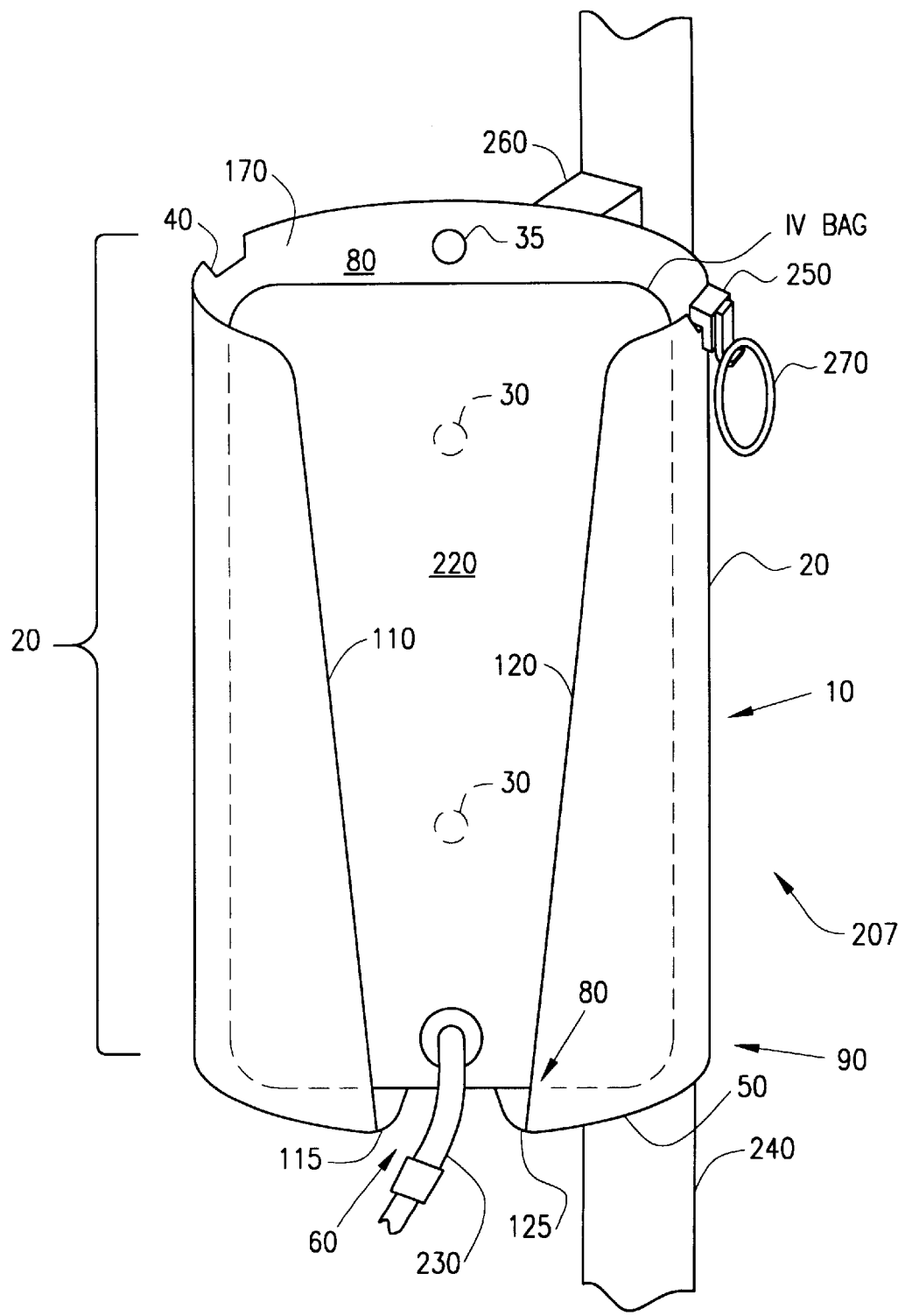
FIG. 6 is a perspective view of an alternative embodiment of the present invention, including an IV containment vessel.

Referring back to FIG. 1, it can be noted that a secondary vessel mounting means 40 appears as a cutout in the upper end 70 of the sleeve 20. This provides for the use of piggyback containment vessels, or bags, which can be hung from the side of the sleeve and located proximate to the upper end 70. As is shown in FIG. 6, a secondary IV hook 250 may be clipped onto the secondary vessel mounting means 40 to provide a simple means for mounting another IV bag on the side of the sleeve 20. Of course, the secondary vessel mounting means 40 may also be used directly with some IV fluid containment vessels that have a hook or other mounting mechanism, such as a snap, built-in. In this case, the corresponding fastener, such as a snap, would also be located on the upper end 70 of the sleeve 20, in the general location of the secondary vessel mounting means 40.

The bottom view of the support apparatus 10 can be seen in FIG. 3. In this case, the base 50 has a generally linear form and the open throat portion 60 is disposed at the convergent end 80 of the longitudinal opening. This form is better suited to accepting the conventional, bulbous, rectangular IV bag. However, it is not as useful for use with IV bottles.

Turning now to FIG. 4, an alternative embodiment of the present invention can be seen. In this case, the apparatus 10 for supporting an intravenous solution containment vessel comprises an elongated, generally circular sleeve 25 constructed in substantially the same fashion as the sleeve 20 shown in FIG. 1. However, instead of having an elliptically-shaped base 50, and an elliptically-shaped upper end 70, or alternatively instead of having an elliptically-shaped base 50 and a circularly-shaped upper end 70, the sleeve 20 illustrated in FIG. 4 has a circularly-shaped base 50 and a circularly-shaped upper end 70. This general cylindrical shape better-accommodates IV bottles, since they are usually manufactured in the form of a right circular cylinder. It may also be advantageous to form the upper end 70 as an ellipse, and the base 50 as a circle, to apply friction pressure to the top end of an IV bottle placed within the sleeve. If the material used to fabricate the support apparatus 10 is flexible, and has the property of retaining its shape (i.e., shape memory), the ellipse at the upper end 70 will tend to re-form around the inverted IV bottle, causing a compressive fit, and better retention of the bottle for protection against movement due to accidental blows or bumps.

While it is believed that the elliptical shape disclosed in FIG. 1 is better-suited to use by both IV bags and IV bottles, it may be that a particular facility utilizes only IV bottles, in which case the circular shape disclosed in FIG. 4 is more appropriate. Essentially, the upper end 70 operates to contain the IV fluid containment vessel placed therein more securely when the shape of the upper end 70 conforms most closely to the shape of the vessel.

Figure 5:
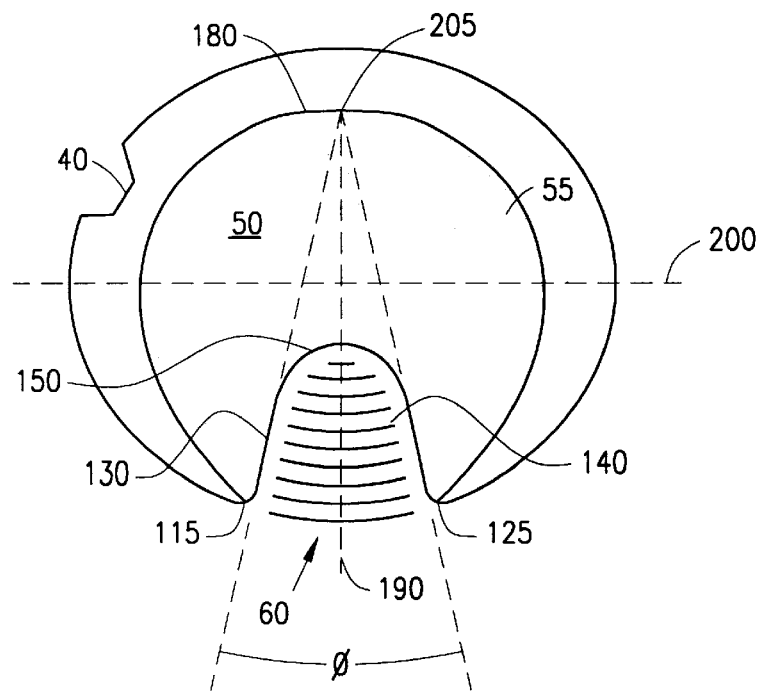
FIG. 5 is a top view of an alternative embodiment of the present invention.

FIG. 5 illustrates a top view of an alternative embodiment of the present invention, which is characterized by a generally circular sleeve 25 shape, as was initially shown in FIG. 4. The existence of a circular base intersection 180 which forms the perimeter of the base 50 is illustrated here, wherein the base intersection 180 is formed along the lines of a base for a right circular cylinder, instead of an elliptical intersection 100, as is shown in FIGS. 1 and 2. The intersections 100 and 180 bound the base area 55, shown in FIGS. 4 and 5.

The throat 60 has an area 210 which is bounded by the left and right throat members 130 and 140, the throat back 150, and a line which extends from the left guide point 115 to the right guide point 125. The base area 55 is preferably from about two to about nine times the throat area 210, and most preferably, the area of the base 50 is about three times the throat area 210. The minor base central axis 190 bisects the area 55 of the base 50, and the major base central axis 200 also bisects the area 55 of the base 50. These axes 190 and 200 are perpendicular to each other. As noted previously, the angular arc Φ is preferably about five degrees to about ninety degrees, but is most preferably about sixty degrees. The distance $D_1$ is preferably about two to about eight times greater than the distance $D_2$, but is most preferably about four times greater than the distance $D_2$.

Turning now FIG. 6, a perspective view of an assembly 207 comprising the support apparatus 10 and an intravenous fluid containment vessel 220, having a fluid spout 230, can be seen. While a commonly available plastic IV bag is shown as the containment vessel 220, an IV bottle, typically made from glass, can also be placed within the support apparatus 10 so as to act as a containment vessel 220.

As shown, the support apparatus 10 in this case is formed as an elongated, generally elliptical sleeve 20; however, a circular sleeve 25 may also be used. The sleeve 20 is attached to the mounting block 260 using the support mounting means 30. In this particular case, simple screws may be inserted through the support mounting means 30 (which may comprise holes or slots) into the mounting block 260. The mounting block 260 is in turn secured to the conventional IV stand 240 by any conveniently available method. As mentioned above, the sleeve 20 may also be fixedly attached to the IV stand 240 itself, or to any other desired location by using the support mounting means 30.

The method of supporting an intravenous containment vessel 220 comprises attaching the intravenous support apparatus 10 to an IV stand 240, wherein the support apparatus 10 has support mounting means 30 fixedly attached to the IV stand 240. The IV containment vessel 220 having a spout 230, is then placed into the support apparatus 10 using a single hand so as to guide the spout 230 between the left and right guide members 110 and 120. The spout 230 is then rested against the open throat 60, and placed so as to protrude from the sleeve 20 at the convergent end 80.

A secondary IV hook 250 may be placed within the secondary vessel mounting means 40 so as to provide a location for hanging an additional piggyback bag 270. As shown, the support apparatus 10 may comprise one or more secondary vessel mounting means 40.

It should be apparent to those skilled in the art that the elliptical sleeve 20 may accommodate standard plastic IV bags, as well as IV bottles. If the sleeve 20 is made from a flexible material, such as ⅛" thick polystyrene, then a frictional fit between an IV bottle and the sleeve 20 will occur, lending additional protection to the bottle and preventing the inadvertent breakage of the bottle by accidental bumps or blows. The support apparatus 10 may be fabricated from several different types of materials including aluminum, stainless steel, cycolac acrylonitrite-butadiene styrene, poly-vinyl chloride, polypropylene, polystyrene, polyethylene, or any clear plastic, including acrylic, most perferrably about ³⁄₁₆" thick.

The shape of the throat 60 will most preferably be wide at the mouth of the throat, indicated by an imaginary line that extends from the left guide point 115 to the right guide point 125, toward the throat back 150, so as to guide the IV containment vessel (i.e., the spout of an IV bag, or the neck of an IV bottle) into a resting place below the central axis of the vessel. However, when the apparatus is used with an IV bag, the depth of the throat may be substantially less, even to the point of being almost nonexistent, since the spout normally protrudes from the front of the bag and rarely into the throat area 210 proper. However, some throat area 210 should be available, since this prevents the operator engaging in the method of the present invention from having to align the spout 230 precisely with the mouth of the throat 60. Further, all corners and edges of the support apparatus 10 should be rounded to prevent cuts, scratches, and abrasions to an IV containment vessel placed therein.

It should also be apparent to those skilled in the art that use of the support apparatus 10 according to the method as disclosed herein provides for single-handed insertion of the containment vessel 220 into the support apparatus 10. This improvement over the prior art saves precious seconds during emergency situations and allows the operator to concentrate on patient problems and not on the physical interface between the containment vessel 220 and the support apparatus 10. Further, the support apparatus 10 is easily moved from location to location by using the alternate mounting means 35, and can be placed practically anywhere a hook or other hanger is available. Further, replacing the containment vessel 220 is also now a single-handed operation.

Although the invention has been described with reference to specific embodiments, this description is not meant to be construed in a limited sense. The various modifications of the disclosed embodiments, as well as alternative embodiments of the invention, will become apparent to persons skilled in the art upon reference to the description of the invention. It is, therefore, contemplated that the appended claims will cover such modifications that fall within the scope of the invention, or their equivalents.

What is claimed is:

1. An apparatus for supporting an intravenous solution containment vessel comprising:

an elongated generally elliptical sleeve having a front, a back with support mounting means, a generally open upper end, and a lower end spaced from the upper end, the front having a left guide member with a lower end disposed at the lower end of the sleeve and a right guide member with a lower end disposed at the lower end of the sleeve, the left and right guide members extending from the upper end to the lower end of the sleeve, said left and right guide members cooperating to define a longitudinal opening along the front of the sleeve and converging from said upper end to a convergent end disposed at said lower end of the sleeve; and a generally closed base which intersects with the front, the back, and the lower ends of the left and right guide members, said base having an open throat portion continuous with the convergent end of the longitudinal opening in the front of the sleeve to form a substantially symmetrical means for centering the spout of the IV bag or bottle such that the spout will fall between the sides of the longitudinal opening in the front of the sleeve and continue through the open throat portion at the convergent end of the sleeve.

2. The support apparatus of claim 1, wherein the base is disposed substantially perpendicular to the sleeve and has a generally elliptical form.

3. The support apparatus of claim 1, wherein the base is disposed substantially perpendicular to the sleeve and has a generally circular form.

4. The support apparatus of claim 1, wherein the base has a generally linear form and the open throat portion is disposed at the convergent end of the longitudinal opening.

5. The support apparatus of claim 1, wherein the throat has a left throat member intersecting the lower end of the left guide member at a left guide point, and a right throat member intersecting lower end of the right guide member at a right guide point, and the base has a minor central axis, wherein the angular arc defined by the left and right guide points and an apex located at the intersection of the minor central axis and the back is about five degrees to about ninety degrees.

6. The support apparatus of claim 1, wherein the throat has a left throat member intersecting the lower end of the left guide member at a left guide point, and a right throat member intersecting lower end of the right guide member at a right guide point, and the base has a minor central axis, wherein the angular arc defined by the left and right guide points and an apex located at the intersection of the minor central axis and the back is about sixty degrees.

7. The support apparatus of claim 1, wherein the distance between the left and right guide members near the sleeve upper end is about two to about eight times greater than the distance between the left and right guide members at the convergent end of the sleeve.

8. The support apparatus of claim 1, wherein the distance between the left and right guide members near the sleeve upper end is about four times greater than the distance between the left and right guide members at the convergent end of the sleeve.

9. The support apparatus of claim 1, wherein the throat has a left throat member intersecting the lower end of the left guide member at a left guide point, and a right throat member intersecting the lower end of the right guide member at a right guide point, the base has a minor central axis and an apex located at the intersection of the minor central axis and the back, and wherein the area of the base is from about two to about nine times the area of the triangle formed by the left and right guide points and the apex.

10. The support apparatus of claim 1, wherein the throat has a left throat member intersecting the lower end of the left guide member at a left guide point, and a right throat member intersecting the lower end of the right guide member at a right guide point, the base has a minor central axis and an apex located at the intersection of the minor central axis and the back, and wherein the area of the base is about three times the area of the triangle formed by the left and right guide points and the apex.

11. The apparatus of claim 1, wherein the left and right guide members are inwardly slanting guide members.

12. An apparatus for supporting an intravenous solution containment vessel comprising:

an elongated generally circular sleeve having a front, a back with support mounting means, a generally open upper end, and a lower end spaced from the upper end, the front having a left guide member with a lower end disposed at the lower end of the sleeve and a right guide member with a lower end disposed at the lower end of the sleeve, the left and right guide members extending from the upper end to the lower end of the sleeve, said left and right guide members cooperating to define a longitudinal opening along the front of the sleeve and converging from said upper end to a convergent end disposed at said lower end of the sleeve; and a generally closed base which intersects with the front, the back, and the lower ends of the left and right guide members, said base having an open throat portion continuous with the convergent end of the longitudinal opening in the front of the sleeve to form a substantially symmetrical means for centering the spout of the IV bag or bottle such that the spout will fall between the sides of the longitudinal opening in the front of the sleeve and continue through the open throat portion at the convergent end of the sleeve.

13. The support apparatus of claim 12, wherein the base is disposed substantially perpendicular to the sleeve and has a generally circular form.

14. The support apparatus of claim 12, wherein the base has a generally linear form and the open throat portion is disposed at the convergent end of the longitudinal opening.

15. The support apparatus of claim 12, wherein the base is disposed substantially perpendicular to the sleeve and has a generally elliptical form.

16. The apparatus of claim 12, wherein the left and right guide members are inwardly slanting guide members.

17. A method of supporting an intravenous (IV) containment vessel, comprising the steps of:

attaching an intravenous support apparatus to an IV stand, the apparatus comprising an elongated generally elliptical sleeve having a front, a back, a generally open upper end, and a lower end spaced from the upper end, the front having a left guide member with a lower end disposed at the lower end of the sleeve and a right guide member with a lower end disposed at the lower end of the sleeve, the left and right guide members extending from the upper end to the lower end of the sleeve, said left and right guide members cooperating to define a longitudinal opening along the front of the sleeve and converging from said upper end to a convergent end disposed at said lower end of the sleeve; and a generally closed base which intersects with the front, the back, and the lower ends of the left and right guide members, said base having an open throat portion continuous with the convergent end of the longitudinal opening in the front of the sleeve to form a substantially symmetrical means for centering the spout of the IV bag or bottle such that the spout will fall between the sides of the longitudinal opening in the front of the sleeve and continue through the open throat portion at the convergent end of the sleeve;

placing an IV containment vessel having a spout into the support apparatus using a single hand so as to guide the spout between left and right guide members; and resting the spout against the open throat.

18. The method of claim 17, wherein the intravenous solution containment vessel comprises an IV bag.

19. The method of claim 17, wherein the intravenous solution containment vessel comprises an IV bottle.

20. A method of supporting an intravenous (IV) containment vessel, comprising the steps of:

attaching an intravenous support apparatus to an IV stand, the apparatus comprising an elongated generally circular sleeve having a front, a back, a generally open upper end, and a lower end spaced from the upper end, the front having a left guide member with a lower end disposed at the lower end of the sleeve and a right guide member with a lower end disposed at the lower end of the sleeve, the left and right guide members extending from the upper end to the lower end of the sleeve, said left and right guide members cooperating to define a longitudinal opening along the front of the sleeve and converging from said upper end to a convergent end disposed at said lower end of the sleeve; and a generally closed base which intersects with the front, the back, and the lower ends of the left and right guide members, said base having an open throat portion continuous with the convergent end of the longitudinal opening in the front of the sleeve to form a substantially symmetrical means for centering the spout of the IV bag or bottle such that the spout will fall between the sides of the longitudinal opening in the front of the sleeve and continue through the open throat portion at the convergent end of the sleeve;

placing an IV containment vessel having a spout into the support apparatus using a single hand so as to guide the spout between left and right guide members; and resting the spout against the open throat.

21. The method of claim 20, wherein the intravenous solution containment vessel comprises an IV bag.

22. The method of claim 20, wherein the intravenous solution containment vessel comprises an IV bottle.

* * * * *